(12) United States Patent
Bromley-Davenport et al.

(10) Patent No.: US 11,464,922 B2
(45) Date of Patent: Oct. 11, 2022

(54) MEDICAMENT DISPENSER DEVICE (71) Applicant: Portal Medical Limited, Derbyshire (GB)

(72) Inventors: Darren Bromley-Davenport, Cheshire (GB); Paul Stevenson, East Yorkshire (GB)

(73) Assignee: Portal Medical Limited, Derby (GB)

(*) Notice: Subject to any disclaimer, the term of this patent is extended or adjusted under 35 U.S.C. 154(b) by 432 days.

(21) Appl. No.: 16/173,780

(22) Filed: Oct. 29, 2018

(65) Prior Publication Data

US 2019/0125989 A1 May 2, 2019

(30) Foreign Application Priority Data

Oct. 31, 2017 (GB) .................................... 1717996

(51) Int. Cl.
*A61M 15/00* (2006.01)
*B05D 5/08* (2006.01)
(Continued)

(52) U.S. Cl.
CPC ........ *A61M 15/0001* (2014.02); *A61M 15/00* (2013.01); *A61M 15/009* (2013.01);
(Continued)

(58) Field of Classification Search
CPC .............. A61M 15/00; A61M 15/0001; A61M 15/0045; A61M 15/0065; A61M 15/009; A61M 2205/0238; A61M 2205/02; A61M 2205/0222; A61M 2205/0233; A61M 2207/00; B05D 1/62; B05D 3/144; B05D 5/02; B05D 5/08; B05D 5/083;
(Continued)

(56) References Cited

U.S. PATENT DOCUMENTS

| 5,788,870 A * | 8/1998 | Nguyen | .................... B05D 1/62 |
| | | | 216/63 |
| 6,532,955 B1 * | 3/2003 | Ashurst | .................. A61K 9/008 |
| | | | 128/200.23 |

(Continued)

FOREIGN PATENT DOCUMENTS

| EP | 0575299 A1 | 12/1993 |
| EP | 0642992 B1 | 3/1995 |

(Continued)

OTHER PUBLICATIONS

Kobayashi, H., Bell, A.T., and Shen, M. "Plasma Polymerization of Saturated and Unsaturated Hydrocarbons" Dec. 11, 1973. Macromolecules 1974, vol. 7, pp. 277-283. (Year: 1973).*

*Primary Examiner* — Valerie L Woodward
*Assistant Examiner* — Paige Kathleen Bugg
(74) *Attorney, Agent, or Firm* — Joseph C. Zucchero; Carolyn S. Elmore; Elmore Patent Law Group, P.C.

(57) ABSTRACT

According to the invention there is disclosed a dispenser device for dispensing a medicament, the device comprising at least one component having a coating that comes into contact with the medicament during storage or use of the device on at least one surface thereof, the coating comprising a cross-linked non-diamond like carbon layer comprising 50 At % hydrogen or less and having an interface with the underlying surface of the component.

24 Claims, 4 Drawing Sheets

(51) Int. Cl.
  *B05D 1/00* (2006.01)
  *B05D 3/14* (2006.01)
  *B65D 83/14* (2006.01)

(52) U.S. Cl.
  CPC .... *A61M 15/0045* (2013.01); *A61M 15/0065* (2013.01); *B05D 1/62* (2013.01); *B05D 3/144* (2013.01); *B05D 5/083* (2013.01); *B65D 83/14* (2013.01); *A61M 2205/0238* (2013.01); *A61M 2207/00* (2013.01)

(58) Field of Classification Search
  CPC .......... B05D 5/086; B05D 7/22; B05D 7/227; B05D 7/222; B05D 7/225
  USPC .................................... 128/203.23
  See application file for complete search history.

(56) References Cited

U.S. PATENT DOCUMENTS

| | | | |
|---|---|---|---|
| 6,686,302 B1 * | 2/2004 | Moser | B05D 1/62 428/300.7 |
| 7,879,418 B1 * | 2/2011 | Komvopoulos | C08J 7/042 428/36.9 |
| 2003/0207057 A1 | 11/2003 | Britto et al. | |
| 2004/0003828 A1 * | 1/2004 | Jackson | H01L 21/76814 134/1 |
| 2013/0019863 A1 * | 1/2013 | Stevenson | B65D 83/54 128/200.23 |

FOREIGN PATENT DOCUMENTS

| | | | | |
|---|---|---|---|---|
| EP | 1066073 B2 | 2/2008 | | |
| GE | P20002266 | 6/2000 | | |
| JP | 2002225170 A | 8/2002 | | |
| WO | 9910560 A1 | 3/1999 | | |
| WO | 2007007995 A1 | 1/2007 | | |
| WO | 2008146022 A2 | 12/2008 | | |
| WO | 2008146024 A2 | 12/2008 | | |
| WO | 2008146025 A2 | 12/2008 | | |
| WO | WO-2008146022 A2 * | 12/2008 | ............... B05D 7/02 |
| WO | 2011104539 A1 | 9/2011 | | |
| WO | 2011104541 A1 | 9/2011 | | |
| WO | WO-2011104541 A1 * | 9/2011 | ............. B65D 83/54 |

* cited by examiner

MEDICAMENT DISPENSER DEVICE

The present invention relates to dispenser devices for dispensing a medicament, methods of manufacturing the same, components of the same and methods of treating a component of the same, with particular, but not necessarily exclusive, reference to dispenser devices for dispensing an inhalation medicament.

It is well known to administer medicaments to a patient by inhalation using pressurised dispenser devices which dispense the medicament in a carrier fluid and/or propellant, commonly as an aerosol. Such devices are often referred to as pressurised metered dose inhalers (pMDIs), and are very commonly used for treating asthma and chronic obstructive pulmonary disease (COPD).

Problems associated with dispenser devices of this kind are absorption of the active medicament on the internal surfaces of the device or a detrimental interaction (unwanted chemical reaction). This in turn can lead to a loss of potency and/or erratic dosing during the shelf-life of the device or dose to dose. In some instances, clustering of drug particles can occur if the active medicament is present as a suspension of particles. One approach that has been adopted in order to reduce the surface absorption of the active drug is to modify the surface properties of the device, and traditionally this has been done by spray-coating with a low energy polymer. However, this process can be difficult to manage, and often the quality of the surface coatings is variable. Long chains of polymeric material with very little crosslinking tend to be deposited on the surfaces of the device, leading to the requirement of relatively thick polymer layers (in the order of 5 to 100 microns) in order to provide an effective barrier to the medicament. Spray coating polymers of this kind typically have less than 10% crosslinking and usually significantly less than 5% crosslinking. The present inventors have realized that increasing the crosslinking density of the barrier can improve the effectiveness of the barrier particularly at lower thickness at the sub micron level.

One approach that has been adopted in order to increase the crosslinking density of the barrier and thus reduce the surface absorption of the active drug is to deposit a low energy polymer or inorganic coating (or combination of the two) by plasma polymerisation. EP1066073 and WO2008/146024 are examples of prior art documents which disclose plasma polymerisation onto various components of the dispenser devices. However, it is recognised that a number of delivery problems can exist with coatings of this type. One problem pertains to devices which use a particulate suspension as the delivery system. These delivery systems can be affected by adherence of the medicament particles to and "caking" of these particulates on the walls of the can or on other surfaces within the dispenser device. This may lead to agglomerations which affect the medicament dose. A second problem is due to autocatalytic degradation of some medicaments through contact with certain materials, in particular metal oxides such as aluminium oxide and magnesium oxide, and other reactions between the components and medicaments such as corrosion or formation of detrimental species by such reaction. Certain components of dispenser devices, in particular the can body, are formed from aluminium, and consequently have an aluminium oxide surface layer which also contains alloying compounds such as magnesium. The material underlying the metal oxides contains metal ions available for migration and interaction only a few nanometres in. In the case of native oxides these ions are available at the near surface less than 5 nm in. Coating such components with a barrier potentially provides a way in which both degradation and with a non-stick barrier the adherence of medicament particles to surfaces might be prevented. However, it is not always necessary to have non-stick properties if degradation and/or corrosion are the only concern with a particular drug (for example, if the drug is present in a solution delivery system and not a suspension). Additionally, the performance of some coatings can be less than optimal for various reasons. One such reason is that coatings may have flaws or pin-holes present which enables medicament molecules present in solution to reach the surface of component parts such as the aluminium oxide surface of a can, where degradation and/or corrosion can take place. Conversion treatments such as anodising do not solve the issue, oxide levels are increased and migratory pathways formed.

Most prior art methods of plasma polymerisation onto the surface of device components use fluorocarbon precursors to directly coat the internal surfaces of the device with a fluorocarbon polymer. However, such techniques require a high power density (0.5 W/cm$^3$) which can be detrimental to coating deposition rate. This is because whilst ions are deposited to form a coating, they are re-sputtered from the surface meaning that unreacted sites spontaneously react with free fluorine produced. This causes premature termination of growing polymer chains resulting in a porous powdery coating having a maximum thickness that does not increase over time. Such a coating actually has high porosity with discrete terminated polymer chains which are in turn easily removable by solvent extraction or contact, for example, with hydrofluoroalkane (HFA) propellants because of their extremely low surface tensions. As a result, the present inventors have found that it is extremely difficult to deposit fluorocarbon polymer coatings with a crosslink density of >60% due to the nature of the self-etching effects in the plasma environment. Such films would also show significant loss of hydrophobicity and/or repellancy as the very nature of crosslinking causes losses in for example CF2 functional groups associated with repellancy.

The present invention, in at least some of its embodiments, addresses the above described problems and needs.

According to a first aspect of the present invention, there is provided a dispenser device for dispensing a medicament, the device comprising at least one component having a coating that comes into contact with the medicament during storage or use of the device on at least one surface thereof, the coating comprising a cross-linked non-diamond like carbon layer comprising 50 At % hydrogen or less and having an interface with the underlying surface of the component. This low atomic ratio of hydrogen results from a high crosslink density in the carbon layer. The high crosslink density improves the integrity of the coating (i.e. reduces the occurrence of flaws or pin-holes in the coating which can cause corrosion of the component and/or degradation of medicaments). This also enables the coating to be deposited much thinner than prior art techniques whilst achieving high barrier properties.

In one embodiment, the carbon layer may comprise 40 At % hydrogen or less, preferably 33 At % hydrogen or less, preferably 25 At % hydrogen or less, more preferably 20 At % hydrogen or less, even more preferably 10 At % hydrogen or less and most preferably 5 At % hydrogen or less. As noted above, it is preferable to reduce the atomic ratio of hydrogen in the carbon layer by increasing the crosslink density and thus the At % of carbon.

Crosslinking in said carbon layer may be at least 80%, preferably at least 90%, more preferably at least 95%. This high crosslink density improves the integrity of the coating and significantly reduces migration and absorption of medicament into/by the deposited layer.

In a preferred embodiment, the carbon layer has a thickness of between 5 nm and 150 nm, preferably 50-150 nm.

Advantageously, the carbon layer may comprise less than about 3 At %, preferably less than about 2 At %, more preferably less than about 1 At % oxygen as measured by X-Ray Photoelectron Spectroscopy (XPS). Generally, the At % oxygen should be as close to zero as the process and grade of precursor and metal used permits. In this way, the possibility of degradation of the medicament is minimised and corrosion performance maximised, by ensuring both complete coverage (no oxygen detected by XPS from underlying oxides) and non-reactivity/attraction to polar oxygen functionalities in the coating.

The coating may comprise a second layer which comes into contact with the medicament during storage or use of the device. In such embodiments, the carbon layer acts as a base barrier layer, interfacing the surface of the component and the second layer acts as a top layer for contacting the medicament. The carbon base layer provides a uniform insulating layer which masks any non-uniformity on the component surface.

Advantageously, the second layer may be hydrophobic. The second layer may be a polymer layer or inorganic layer. Preferably, the second layer is a plasma polymerised polymer layer.

The second layer may be a fluorocarbon polymer layer, for example but not limited to, a per-fluorocarbon layer. The internal surface after application of a carbon layer can adopt a uniform floating potential or charge which allows for a uniform thin film of fluorocarbon to be formed, either by reaction with fluorine ions to produce a plasma functionalised surface or deposition of $C_xF_y$ ions from the plasma. This results in a hydrophobic repellent surface with low surface energy and high barrier properties.

In embodiments where the second layer is a fluorocarbon polymer layer, the fluorocarbon polymer layer has a fluorine:carbon ratio of between 1:1 and 1.95:1. The fluorine:carbon ratio is preferably 1.25:1 to 1.8:1. This fluorine:carbon ratio is higher than would typically be observed in a straight plasma fluorocarbon coating (i.e. without the carbon base layer which interacts with the surface of the component).

The second layer may have a thickness of between 1 nm and 100 nm, preferably between 1nm and 60 nm, more preferably between 1 nm and 25 nm, most preferably between 1 nm and 15 nm. The carbon layer enables a thin fluorocarbon film to be deposited which because of the underlying carbon film provides the desired barrier properties where a fluorocarbon film of the same thickness would most definitely not. Thus, a thin coating of high integrity can be achieved.

Advantageously, the fluorocarbon polymer layer may comprise less than about 2 At %, preferably less than about 1 At %, more preferably less than about 0.9 At % oxygen as measured by XPS. As noted above, it is preferable to have the At % as low as possible in the coating to minimise the possibility of degradation of the medicament and maximise corrosion performance.

In one embodiment, the second layer has an interface with the carbon layer. Preferably, the interface between the carbon layer and the second layer is graded. This grading results in a highly covalent integral structure showing inherently strong cohesive strength properties, impermeable to HFA and other organic solvents. The carbon to second layer gradient is preferably over a graded thickness of 1-75 nm, more preferably 1-40 nm and most preferably 1-15 nm.

The coating may have a water contact angle of between 115° to 130°. Thus, the coating has a highly repellent, hydrophobic surface.

Preferably, crosslinking in said second layer is at between 75% and 35%.

The dispenser device may be in the form of a pressurised dispenser device which dispenses the medicament in a carrier fluid. For example, the dispenser may be a pressurised metered dose inhaler. At least one component may be a metallic component or a polymeric component. The component may be a metallic can body. However, other components of the dispenser devices, such as valve stems and springs are also included.

In one embodiment, the at least one component is formed from aluminium. In particularly preferred embodiments, the metallic component is an aluminium can body. Alternatively, the metallic component may be formed from stainless steel.

In embodiments where the at least one component is formed of aluminium, advantageously, the at least one surface having a coating thereon does not turn black on exposure to acidified copper sulphate. Aluminium turns black on exposure to acidified copper sulphate due to reaction with aluminium/aluminium oxide causing precipitation of copper at the reaction site (pin-hole of other exposed areas). Therefore, the at least one surface having a coating thereon does not react with the acidified copper sulphate demonstrating a high integrity coating without pin holes.

In one embodiment, the at least one component is a can body and the interior surface of the can body has said coating.

Preferably, the medicament is an inhalation medicament.

According to a second aspect of the invention there is provided a component for a dispenser device, the component comprising a coating that comes into contact with the medicament during storage or use of the device on at least one surface thereof, the coating comprising a cross-linked non-diamond like carbon layer comprising 50 At % hydrogen or less and having an interface with the underlying surface of the component.

Unless the context dictates otherwise, the various preferred features and options of the first aspect apply equally to the second aspect.

According to a third aspect of the present invention, there is provided a method of treating a component of a medicament dispenser device comprising at least one surface that comes into contact with a medicament during storage or use of the device including the steps of:

providing said component; and coating at least one of said surfaces with a coating comprising a cross-linked non-diamond like carbon layer having a hydrogen content of 50% or less and having an interface with the at least one surface of the device.

The carbon layer is preferably formed by a plasma processing step which comprises creating a plasma of at least one hydrocarbon monomer. The hydrocarbon monomer may be alkanes of the formula $C_nH_{2n+2}$ where n is 1 to 12. Methane and ethane are particularly preferred. $C_3H_8$, $C_4H_{10}$ and $C_5H_{12}$ are also preferred embodiments. Alkenes, alkynes and cyclic hydrocarbons may be used as the precursor.

In preferred embodiments, the coating comprises a second layer which comes into contact with the medicament during storage or use of the device, wherein the second layer is formed by plasma deposition. Advantageously, the carbon layer may directly interface the second layer. Preferably, the interface between the carbon layer and the second layer is graded.

The plasma deposition of the second layer may comprise plasma polymerising at least one monomer. The at least one monomer may be a fluorocarbon monomer, preferably a per-fluorocarbon monomer. Suitable per-fluorocarbon precursors include CnF2n+2 where n is in the range 1 to 16, preferably in the range 1 to 6, and the chemicals HFA134a (1,1,1,2,-tetrafluoroethane) and HFA227 (1,1,1,2,3,3,3-heptafluoropropane), which are commonly used as propellants in medicament dispenser devices. Other propellants such as HFA 152a (1,1-Difluoroethane), R32 and Hydrofluro-Olefins (HFO's) may also be used. Cyclic per-fluorocarbons or unsaturated per-fluorocarbons may be used. Particularly preferred embodiments are CF4 and C4F8. Precursors are preferably small because the proportion of fluorine is greater and greater number of CF2 groups can be formed.

Grading between the carbon layer and the second layer may be achieved by ramping down the hydrocarbon monomer whilst ramping up the fluorocarbon (or other) monomer that is plasma polymerised to form the second layer.

In one embodiment, at least part of the coating step is performed under DC bias control. Preferably, the plasma ionisation of at least one hydrocarbon monomer and the plasma deposition of the second layer are performed under DC bias control and the plasma ionisation of at least one hydrocarbon monomer is performed using a higher DC bias voltage than the plasma deposition of the second layer. This prevents etching of the carbon layer and thus maintains coating integrity and a high degree of crosslinking.

Preferably, the plasma deposition of the second layer is performed using a DC bias voltage of less than 60 volts, preferably less than 50 volts, more preferably less than 40 volts. The low DC bias voltage prevents etching of the carbon layer and thus maintains coating integrity and a high degree of crosslinking.

Preferably, the plasma ionisation of at least one hydrocarbon monomer is performed using a DC bias voltage of between 1 and 150 volts, preferably between 30 and 80 volts, more preferably between 50 and 75 volts.

In a preferred embodiment, at least part of the coating step is performed using a power density in the range 0.01 to 0.05 Wcm-2, preferably 0.02 to 0.03 Wcm-2. This low power density is beneficial for coating deposition rate and for coating integrity. This is because there is no re-sputtering or etching of the coating which can otherwise cause termination of growing polymer chains.

Advantageously, at least part of the coating step may be performed using a process pressure in the range of $9 \times 10^{-1}$ mbar and $2 \times 10^0$ mbar. This high pressure increases the deposition rate of the coating.

Preferably, the method further comprises a cleaning step prior to the coating step. This removes any pre-process hydrocarbons or ubiquitous contaminants from the surface of the component and etches away any surface asperities, leaving the resulting surface clean and dramatically functionalised.

According to a fourth aspect of the present invention, there is provided a dispenser device for dispensing a medicament, the device comprising at least one component having a coating on at least one surface thereof, the coating comprising a carbon base layer having an interface with the underlying surface of the component and a second layer which comes into contact with the medicament during storage or use of the device.

According to a fifth aspect of the present invention, there is provided a component for a dispenser device comprising a coating on at least one surface thereof, the coating comprising a carbon base layer having an interface with the underlying surface of the component and a second layer which comes into contact with the medicament during storage or use of the device.

Unless the context dictates otherwise the various preferred features and options of the first and second aspect of the present invention apply equally to the fourth and fifth aspect of the present invention.

According to a sixth aspect of the present invention, there is provided a method of treating a component of a medicament dispenser device comprising at least one surface that comes into contact with a medicament during storage or use of the device including the steps of:

providing said component;

coating at least one of said surfaces with a coating comprising a carbon base layer having an interface with the underlying surface of the component and a second layer which comes into contact with the medicament during storage or use of the device.

Unless the context dictates otherwise the various preferred features and options of the third aspect of the present invention apply equally to the sixth aspect of the present invention.

According to a seventh aspect of the present invention, there is provided a method of manufacturing a medicament dispenser device, the method comprising treating a component in accordance with the method of the third aspect or the sixth aspect of the present invention, providing other components of the device and assembling the components to provide an assembled medicament dispenser device.

Embodiments of the present invention will now be described, by way of example only, with reference to the accompanying drawings, in which.

Figure 1:
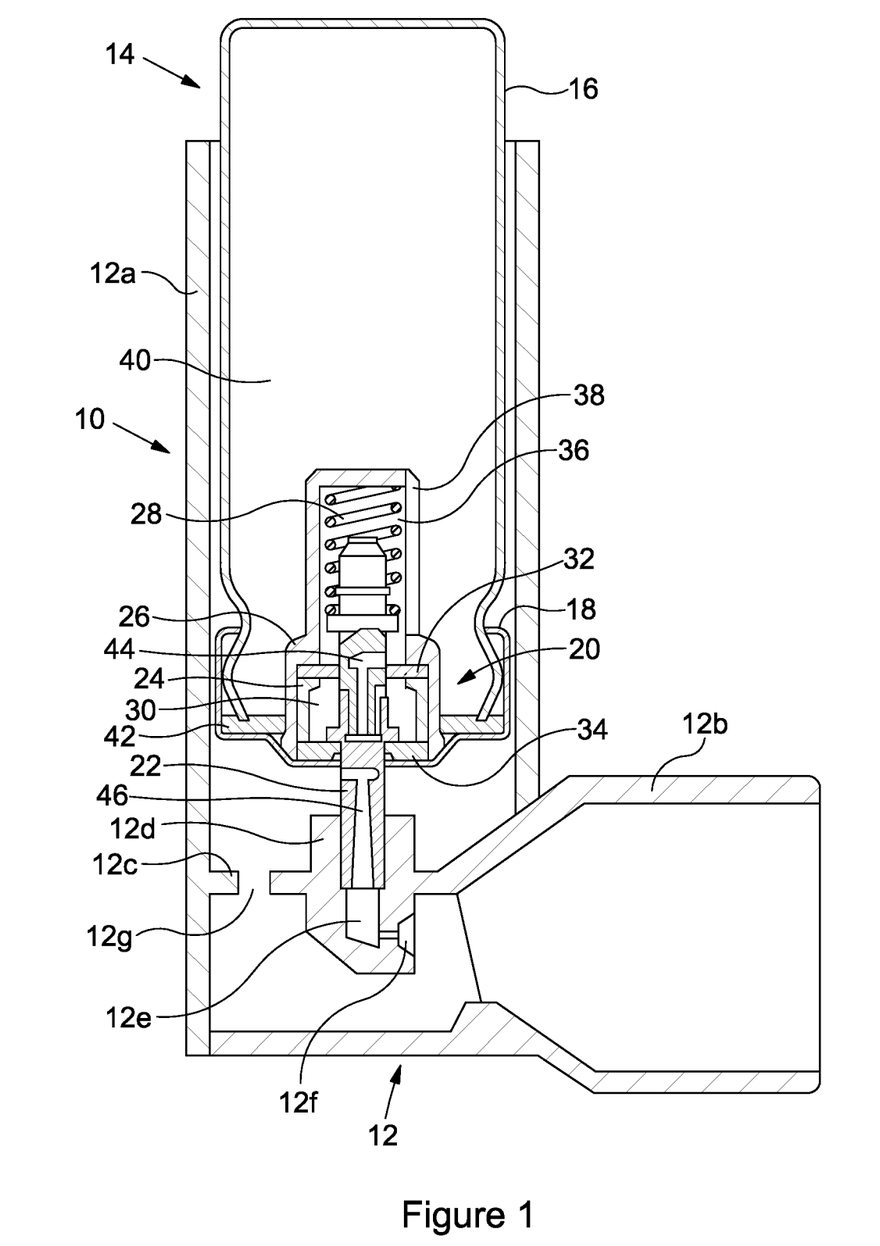
FIG. 1 is a cross sectional view of a pressurised dispenser device.

FIG. 1 depicts a pressurized dispenser device, shown generally at 10, which comprises a housing 12 which receives a pressurized medicament containing arrangement 14. The housing 12 comprises an open ended cylindrical portion 12*a* in which the pressurized medicament containing arrangement 14 is disposed, and an open ended passage 12*b* which serves as a mouthpiece. The housing 12 further comprises an inner wall 12*c* which supports a socket 12*d* having a passageway 12*e* which receives the valve stem of the pressured medicament container arrangement. The passageway 12*e* communicates with an opening 12*f* which in turn is in communication with the exit passage defined by open ended passage 12*b*. The inner wall 12*c* has a number of apertures 12*g* formed therein which permits air to flow from the upper area of the housing 12 into the open ended passage 12*b*.

The structure and operation of the pressurized medicament container arrangement 14 will now be described in more detail. The arrangement 14 comprises a can body 16 on which is crimped a ferrule 18. Mounted on the ferrule 18 is a metering valve system, shown generally at 20. The metering valve system 20 comprises a valve stem 22, a portion of which is disposed in a valve member 24. The valve stem 22 and valve member 24 are both located in a valve housing 26, and the valve stem 22 is axially reciprocable therein against the action of a spring 28 which biases the valve stem 22 into a closed position as shown in FIG. 1.

The metering valve system 20 further comprises a metering chamber 30 which is defined by the valve member 24 and a portion of the valve stem 22 together with inner and outer seals 32, 34. The inner seal 32 acts to seal the valve member 24 against the valve housing 26, and separates the metering chamber 30 from the interior 36 of the valve housing 26. The outer seal 34 acts to seal the valve member 24 and valve housing 26 against the ferrule 18, and also seals the metering chamber 30 from the outside of the pressurized medicament container arrangement 14. Further sealing is provided by a can body seal 42 which acts to seal the can body 16 against the ferrule 18 upon crimping of same. The valve housing 26 has a plurality of slots 38 which enable the interior 36 of the valve housing 26 to communicate with the interior 40 of the can body 16. The valve stem 22 has two channels 44, 46. Each channel, 44, 46 comprises a longitudinal passageway and a transverse passageway. The transverse passageway of the valve stem channel 44 is disposed so that, when the pressurized medicament container arrangement 14 is in its closed position as shown in FIG. 1, the metering chamber 30 is in communication with the interior 36 of the valve housing 26 and thus is also in communication with the interior 40 of the can body 16. As explained in more detail below, the volume of the metering chamber 30 corresponds to the volume of medicament containing fluid administered in a single dose. In the closed position shown in FIG. 1, the dose is wholly contained in the metering chamber 30 and cannot escape to the outside of the pressurized medicament container arrangement 14 owing to the action of the outer seal 34.

To release a dose of medicament containing fluid, the valve stem 22 is pushed against the biasing action of the spring 28 into the interior 36 of the valve housing 26 to an extent that the valve stem channel 44 no longer communicates with the metering chamber 30. The valve stem 22 is designed so that, in this dispensing position, the valve stem channel 46 of the valve stem 22 communicates with the metering chamber 30, thereby allowing the dose of medicament containing fluid in the metering chamber 30 to be dispensed through the valve stem 22. The dose then passes through the passageway 12e, opening 12f and open ended passage 12b to exit the device.

When the valve stem 22 is subsequently released the biasing action of the spring 28 causes the valve stem 22 to move back towards the position shown in FIG. 1. Thus, the valve stem channel 46 assumes a position whereby the metering chamber 30 is sealed against the outside, and the valve stem channel 44 assumes a position whereby the interior 36 of the valve housing 26 is in communication with the metering chamber 30. Owing to the pressure differential between the relatively high pressure interior 40 of the can body 16 and the relatively low pressure of the metering chamber 30, the metering chamber 30 is refilled with another dose of the medicament containing fluid.

The pressurized dispenser device 10 shown in FIG. 1 is one example of such a device, and many other metering arrangements are known which differ to a greater or lesser degree in their precise mode of action. The present invention does not lay claim to the mode of action of the device shown in FIG. 1 or of any other pressurized dispenser device. Rather, the present invention provides devices and components for same which are treated so as to inhibit losses of medicaments to internal surfaces of the device, and associated methods of production of such devices and components. The device shown in FIG. 1 is provided in order to assist the reader's appreciation of how the present invention might be applied. The skilled reader will appreciate that the present invention can be applied to other designs of pressurized dispenser device than the one shown in FIG. 1, and indeed can be applied to different types of medicament dispenser devices than pressurized dispenser devices.

Figure 2:
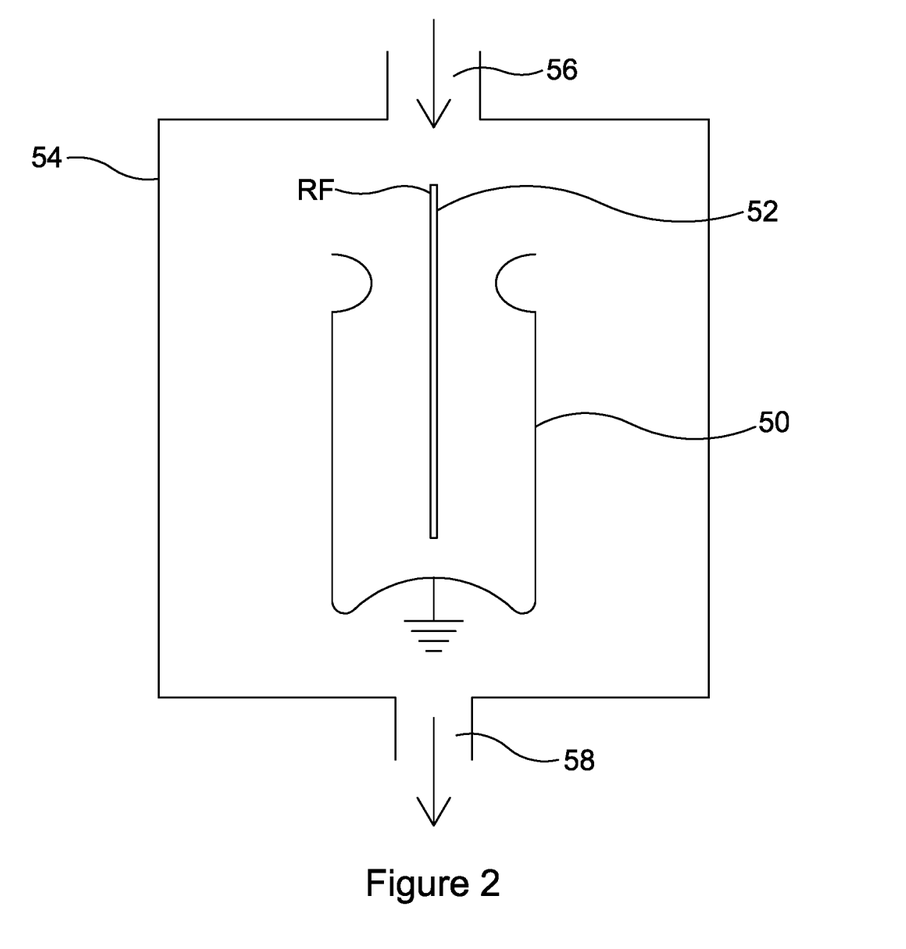
FIG. 2 shows an arrangement for coating a can body.

The present invention provides methods for depositing coatings which inhibit losses of the medicament to the internal surfaces of the pressurized dispensing device by providing highly crosslinked plasma polymerised coatings. The present inventors have found that coatings having higher crosslink densities can be deposited much thinner than those with lower crosslink densities whilst still achieving optimum barrier properties. FIG. 2 shows an arrangement in which a can body 50 is coated by plasma deposition. In the arrangement, the can body 50 is maintained at earth and an elongate RF electrode 52 extends into the interior of the can body 50 substantially along the longitudinal axis of the can body 50. The can body 50 is positioned in a plasma reactor 54 which has a gas/monomer feed inlet 56, and an outlet 58 for exhausting gasses using a vacuum pump (not shown). The appropriate monomer or monomers are delivered into the can body 50 by the gas inlet 56 from an appropriate delivery source (not shown) which typically includes one or more mass flow controllers. Power densities in the range of 0.01 to 0.05 $W/cm^2$, typically of around 0.02 $W/cm^2$ or 0.03 $W/cm^3$ may be employed. These relatively low power densities are beneficial to coating deposition rate and also increase the cross-link density of the deposited coatings. This is because the re-sputtering from the coating surface and resulting premature termination of growing polymer chains caused by high power densities is avoided.

Initially, oxygen and argon are flowed into the plasma reactor 54 by the gas inlet 56 to purge the plasma reactor 54. A process pressure in the range of $5 \times 10^{-2}$ to $2 \times 10^0$ mbar, typically $1.3 \times 10^0$ mbar is used. Once the plasma reactor 54 has been purged of unwanted gasses, the can body 50 undergoes a pre-cleaning step wherein the supply of oxygen and argon is maintained at a constant flow rate and the process pressure is also maintained. Power is supplied to the RF electrode 52 and a plasma is struck using techniques well known in the art. The interior surfaces of the can body 50 are pre-cleaned with the mixture of argon and oxygen using both reactive ion etching and sputtering to remove any pre-process hydrocarbons, organic components and surface inspirations from the surface of the component. This process is controlled using a DC bias voltage of greater than 50 volts, and preferably greater than 150 volts. The resulting interior surfaces of the can body 50 are both clean and functionalzsed to enable the subsequent carbon overlay to reactively bond with the prepared surface.

Once the interior surfaces of the can body 50 have been cleaned, the supply of oxygen and argon to the plasma reactor 54 via the gas inlet 56 is stopped and the system is evacuated to a low vacuum pressure of $1 \times 10^{-3}$ mbar to remove residual oxygen. Residual oxygen can be detrimental to the build up of deposited coatings and their adhesion as it can act to reactively ion etch the deposited coating by combination with carbon to form CO and $CO_2$ which are readily pumped out of the plasma reactor 54 via the gas outlet 58.

Hydrocarbon pre-cursors, such as methane, ethane, propane, butane, pentane etc. are then flowed into the plasma reactor 54 through the gas inlet 56 and the pressure in the plasma reactor 54 is increased back up to around $1.3 \times 10^0$ mbar. The flow of hydrocarbon pre-cursors is initially ramped up over a defined period. Gas pressures in the range of $5 \times 10^{-2}$ mbar and $2 \times 10^0$ mbar can be used. These relatively high pressures increase the rate of deposition of the carbon coating. A highly crosslinked non-diamond like carbon coating is deposited onto the interior surfaces of the can body 50 by striking and maintaining a plasma whilst the hydrocarbon pre-cursors are flowed into the can body 50. Typically 13.56 MHz RF power is applied to the RF electrode 52, and a plasma is struck using a technique well known in the art. Other RF frequencies may be used, and it is anticipated that frequencies in the range of 4 kHz to 20 MHz may be utilized either in continuous power or pulsed mode.

With the configuration shown in FIG. 2, with the RF electrode 52 positioned in the earthed can body 50, the effective electrical resistance of the can body 50 increases as the internal surface of the can body 50 gets progressively coated. As a result, the normal electron path to the earthed can body 50 is reduced as the coating thickness increases. Forward power operation is typically used in prior art plasma polymerization processes for coating components, such as can bodies, for medicament dispenser devices. However, under normal forward power operation, electron emission from the power supply will be reduced as the processing proceeds, self DC bias will be reduced, and plasma intensity will drop, resulting in a loss of crosslink density which is detrimental to coating properties and can lead to a weak, porous coating. In contrast, by operating a DC bias control, the DC bias is fixed, and a constant electron emission is maintained which in turn maintains a constant plasma density. This provides a constant deposition rate, and a high quality, uniform coating, with increased crosslink density. Furthermore, DC bias can be ramped in relation to the deposition rate and time to control the thickness of the coating with constant crosslink density, both in terms of lateral extent of the coating and in terms of depth of the coating, which would not otherwise be achieved in forward power mode. As such, a highly crosslinked non-diamond like carbon coating is deposited by operating a DC bias control. This DC bias control provides a constant deposition rate, and a high quality, uniform coating. This steady rate of coating can be maintained until a desired thickness is obtained. Typically the desired thickness will be in the range of 5 to 150 nm and the carbon polymer coating will be a highly crosslinked (at least 90%), highly reactive coating on the surface of the can body 50. The carbon polymer layer also provides a uniform, insulating layer which masks any non-uniformity on the surface of the can body 50. The internal surface of the can body 50 after application of a carbon polymer layer can adopt a uniform floating potential or charge which allows for a uniform thin film of fluorocarbon to be formed in the following stage of processing, either by reaction with fluorine ions in the plasma or deposition of $CxF_y$ ions from the plasma. This uniform charge is crucial for uniform deposition and is not achievable without the insulating carbon layer.

Once the desired thickness of the highly cross-linked non-diamond like carbon layer has been obtained, fluorocarbon monomers are introduced into the can body 50 via the gas inlet 56. The fluorocarbon monomers can either be instantaneously introduced accompanied by a cut-off in the supply of hydrocarbon monomers, mixed with the hydrocarbon monomers, or ramped in over time. It is preferred that the fluorocarbon monomer supply is ramped up over time whilst the hydrocarbon monomer supply is ramped down such that the interface between the carbon layer and the fluorocarbon polymer layer is graded i.e. there is no distinct boundary between the two. The highly reactive carbon polymer coating already deposited on the interior surface of the can body 50 reacts with the free fluorine produced in the fluorocarbon plasma, resulting in a fluorocarbon layer immediately overlaying the carbon layer. In addition, this stage is accompanied by significantly ramping down the DC bias. This prevents etching of the carbon layer. The pressure in the plasma reactor 54 is maintained at between $9 \times 10^1$ and $1.3 \times 10^0$ mbar and this relatively high pressure compared to prior art processes results in an increased rate of formation of the fluorocarbon layer.

The fluorocarbon layer is built up until a minimum thickness is obtained. Typically, the thickness of the fluorocarbon layer will be in the range of 1-15 nm when using $CF_4$ as the hydrocarbon precursor or around 16-100 nm when using $C_4F_8$ as the hydrocarbon precursor. Without the highly cross-linked carbon barrier layer deposited on the surface of the can body 50, a fluorocarbon layer with a thickness of 1-15 nm or even 1-100 nm would clearly not be sufficient to form an integral barrier alone. The fluorine: carbon ratio in the fluorocarbon layer is also typically much higher than that observed in a straight fluorocarbon plasma process (1.5:1 to 1.95:1 compared to 1:1 to 1.5:1), resulting in a high $CF_2$ content. This achieves a hydrophobic repellent surface with high barrier properties which comes into contact with the medicament during storage and use of the device. The resulting carbon polymer layer deposited on the interior surface of the can body 50 and fluorocarbon polymer layer deposited on the surface of the hydrocarbon polymer layer results in a highly covalent integral coating demonstrating inherently strong cohesive strength properties, impermeable to HFA and other organic solvents.

Once the fluorocarbon polymer layer reaches the desired thickness, the supply of fluorocarbon monomers to the plasma reactor via the gas inlet 56 is stopped and the system is evacuated to a low vacuum pressure of $1 \times 10^{-3}$ mbar to remove any residual monomers via the gas outlet 58.

Aluminium can bodies coated using the above method have shown water contact angles of between 115° to 130°. XPS spectra of the coatings show the carbon polymer layer to have less than 2% $O_2$ content and the fluorocarbon polymer layer to have less than 1% $O_2$ content. XPS spectra also show crosslinking in the carbon coating of at least 95% when using pre-cursors such as methane, ethane and ethylene and crosslinking of greater than 55% in the fluorocarbon polymer layer.

It is preferred that the fluorocarbon monomers used as precursors for the fluorocarbon polymer layer are small because the proportion of fluorine: carbon is higher. It is preferred that the monomers are one of $CF_4$ or $C_4F_8$, however, other suitable precursors include $C_2F_6$, $C_3F_8$, $C_5F_{10}$, HFA134a, HFA227 or HFA 152a. The hydrocarbon precursors can be any hydrocarbon monomer, including methane, ethane, propane, butane, pentane, hexane etc.

EXAMPLE 1

The arrangement shown in FIG. 2 and described above was used to deposit a coating on the interior surface of an aluminium can body which inhibits losses of medicament to the internal surfaces of the can body by providing highly crosslinked plasma deposited coatings. Table 1 shows the process conditions at various stages of surface modification of an aluminium can body according to an exemplary embodiment of the present invention.

TABLE 1

| Stage | Power Range | Pressure Range | Flow Range |
|---|---|---|---|
| Cleaning Reactive Ion Etching and/or sputtering. | 50-3000 W Controlled dc bias >50-150 V | $1e^{-1}$-$3e^{0}$ mbar | 20-400 sccm $O_2$, Ar and/or $CF_4$ |
| Carbon Barrier Coating | dc bias 1-150 V | $1e^{-1}$-$3e^{0}$ mbar | 20-350 sccm $C_xH_y$ |
| Fluorocarbon Surface Layer | dc bias 1-100 V | $1e^{-1}$-$3e^{0}$ mbar | 20-350 sccm $C_xF_y$ |

A random sample of canisters having coatings formed by the above method were subjected to a copper sulphate test to examine the coating integrity. During the copper sulphate test, each of the canisters was filled with acidified $CuSO_4$ up to the brim level and left for 1 minute. The $CuSO_4$ was then removed and the canisters were opened to visually analyse and grade the level of copper sulphate reaction. Evidence of copper sulphate reaction is easy to identify as aluminium turns black on exposure to acidified $CuSO_4$ due to the precipitation of copper at exposed aluminium sites.

Figure 3A:
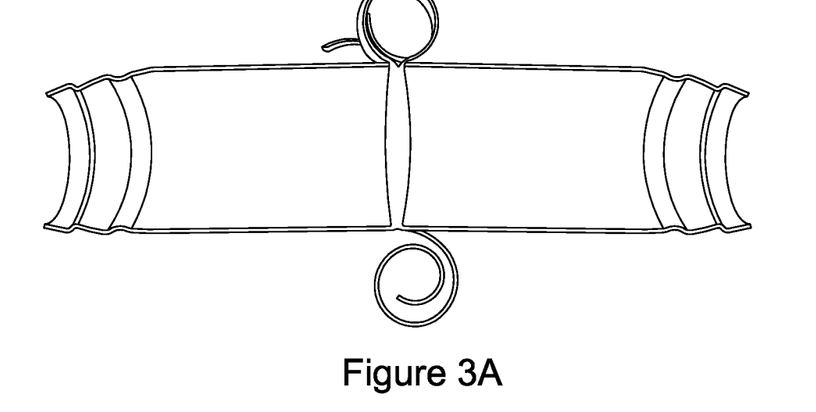
FIG. 3A shows a dissected aluminium can body that has been subjected to a copper sulphate test and has had a negative reaction with copper sulphate after 1 minute.
Figure 3B:
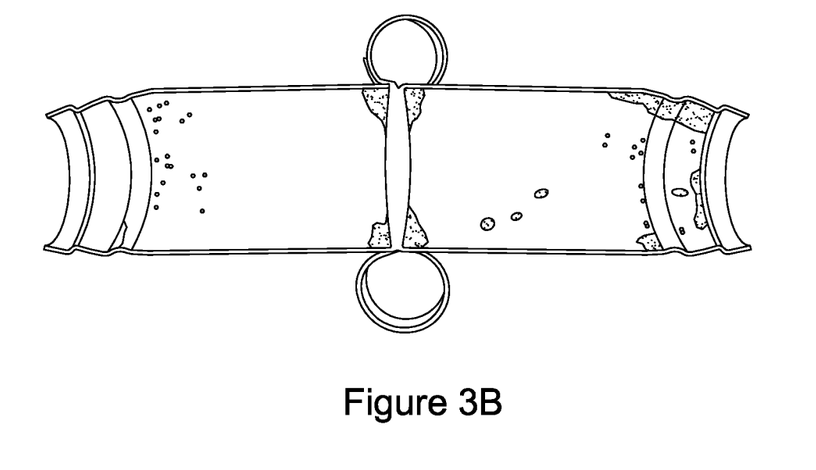
FIG. 3*b* shows a dissected aluminium can body that has been subjected to a copper sulphate test and has had a fine particle reaction with copper sulphate after 1 minute.
Figure 3C:
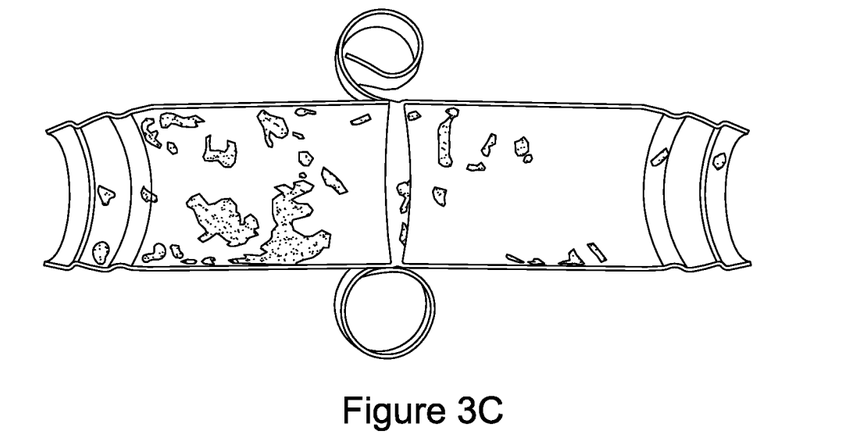
FIG. 3*c* shows a dissected aluminium can body that has been subjected to a copper sulphate test and has had a partial reaction with copper sulphate after 1 minute.
Figure 3D:
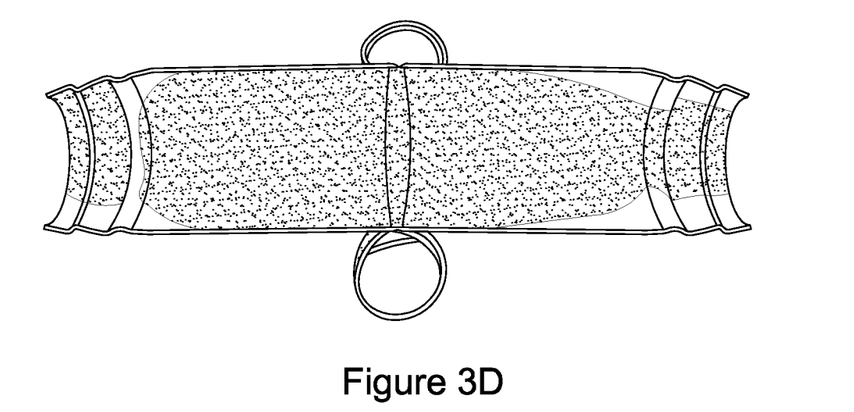
FIG. 3*d* shows a dissected aluminium can body that has been subjected to a copper sulphate test and has had a full reaction with copper sulphate after 1 minute.

FIG. 3A shows an aluminium canister having a coating with high integrity, i.e. no pin holes, that has had a negative reaction with copper sulphate. FIG. 3B shows an aluminium canister that has undergone a fine particle reaction with copper sulphate due to the presence of pin holes. FIG. 3C shows an aluminium canister that has undergone a partial reaction with copper sulphate due to a low integrity coating. FIG. 3D shows an aluminium canister without a coating that has undergone a full reaction with copper sulphate.

The images show that if the coating is deposited without the correct level of crosslinking by plasma means or if the coating density is not sufficient, integrity of the coating is significantly compromised as seen by pin holing and high levels of aluminium attack. All of the canisters having coatings formed by the above method demonstrated high integrity coatings that did not react with acidified copper sulphate, i.e., the canisters corresponded to the canister shown in FIG. 3A.

EXAMPLE 2

The process described in example 1 was then repeated using $CF_4$ as the fluorocarbon precursor instead of $C_4F_8$. When using $CF_4$ as a fluorocarbon precursor, it is possible to deposit a thinner fluorocarbon polymer layer of 1-15 nm having comparable hydrophobic barrier properties to the fluorocarbon polymer layer produced using $C_4F_8$ as a fluorocarbon precursor (60-100 nm). This is because of the higher fluorine:carbon ratio. The XPS data for each of the coatings is compared in Table 2 below.

TABLE 2

| Element (%) | CF4 | C4F8 |
|---|---|---|
| Mg | 0 | 0 |
| F | 56.64 | 59.26 |
| O | 0.46 | 0.82 |
| N | 0 | 0 |

TABLE 2-continued

| Element (%) | CF4 | C4F8 |
|---|---|---|
| C | 42.89 | 39.92 |
| Al | 0 | 0 |

The coatings produced each comprised less than 1% $O_2$. Each of the coatings had a fluorine:carbon ratio of between 1.3 and 1.5.

The Carbon is spectra for each of the canister coatings is compared in Table 3.

TABLE 3

| Species % | CF4 | C4F8 |
|---|---|---|
| CF3 | 11.8 | 19.5 |
| CF2 | 25.1 | 24.3 |
| CF | 13.5 | 12.2 |
| C—CF | 22.7 | 28.2 |
| C—C | 26.8 | 15.7 |

It can be seen that when using $CF_4$ as the fluorocarbon precursor, there is a much higher $CF_2$:$CF_3$ ratio. Without wishing to be bound to any theory or conjecture, the present inventors believe that this is either due to an increased polymer chain length or an increased proportion of free fluorine in the plasma reacting with the carbon barrier base layer.

It will be apparent to a person skilled in the art, from the foregoing description, that modifications and variations can be made to the described embodiment without departing from the scope of the invention as defined in the claims. For example, the highly cross-linked non-diamond like carbon barrier layer does not have to be coated with a fluorocarbon layer. Instead, the carbon layer may be coated with a silicon layer, or indeed any hydrophobic or other layer. Alternatively, the highly cross-linked non-diamond like carbon barrier layer can be used alone to effectively prevent absorption of the medicament onto the surface of the device and does not require a top layer or coating.

In addition, whilst this embodiment discloses coating an aluminium can body, the coating may be deposited any polymeric or metallic components used for dispensing medicaments and provides an effective barrier for preventing absorption of the medicament onto the surface of the component.

The invention claimed is:

1. A dispenser device for dispensing a medicament, the device comprising at least one component having a coating that comes into contact with the medicament during storage or use of the device on at least one surface thereof, the coating comprising a cross-linked non-diamond like, non-fluorinated carbon layer consisting of carbon, 50 At % hydrogen or less and less than about 3 At % oxygen as measured by XPS and having an interface with the underlying surface of the component, wherein the crosslinking in said carbon layer is at least 80%.

2. A dispenser device according to claim 1, wherein the carbon layer comprises 10 At % hydrogen or less.

3. A dispenser device according to claim 1, wherein the carbon layer has a thickness of between 5 nm and 150 nm.

4. A dispenser device according to claim 1, wherein the coating comprises a second layer which comes into contact with the medicament during storage or use of the device.

5. A dispenser device according to claim 4, wherein said second layer is at least one of a hydrophobic layer, a polymer layer or an inorganic layer.

6. A dispenser device according to claim 4, wherein crosslinking in said second layer is at least 50%.

7. A dispenser device according to claim 1 in the form of a pressurised dispenser device which dispenses the medicament in a carrier fluid.

8. A dispenser device according to claim 1 wherein the at least one component is a metallic component or a polymeric component.

9. A dispenser device according to claim 1, wherein the at least one component is a can body, in which the interior surface of the can body has said coating.

10. A dispenser device according to claim 1, wherein the medicament is an inhalation medicament.

11. A method of treating a component of a medicament dispenser device comprising at least one surface that comes into contact with a medicament during storage or use of the device including the steps of: providing said component; coating at least one of said surfaces with a coating comprising a cross-linked non-diamond like carbon layer having a hydrogen content of 50% or less and less than about 3 At % oxygen as measured by XPS and having an interface with the at least one surface of the device, wherein the crosslinking in said carbon layer is at least 80%.

12. A method according to claim 11, wherein said carbon layer is formed by a plasma processing step which comprises creating a plasma of at least one hydrocarbon monomer.

13. A method according to claim 11, wherein the coating comprises a second layer which comes into contact with the medicament during storage or use of the device, wherein the second layer is formed by plasma deposition.

14. A method according to claim 13, wherein the plasma deposition of the second layer comprises plasma polymerising at least one monomer.

15. A method according to claim 14, wherein said at least one monomer is a fluorocarbon monomer.

16. A method according to claim 11, wherein at least part of the coating step is performed under DC bias control.

17. A method according to claim 16 wherein the coating comprises a second layer which comes into contact with the medicament during storage or use of the device, wherein the second layer is formed by plasma deposition, and wherein the plasma processing step and the plasma deposition of the second layer are performed under DC bias control and the plasma processing step is performed using a higher DC bias voltage than the plasma deposition of the second layer.

18. A dispenser device for dispensing a medicament, the device comprising at least one component having a coating on at least one surface thereof, the coating comprising a cross-linked non-diamond like, non-fluorinated carbon base layer consisting of carbon, 50 At % hydrogen or less and less than about 3 At % oxygen as measured by XPS and having an interface with the underlying surface of the component, wherein the crosslinking in said carbon layer is at least 80% and a second layer which comes into contact with the medicament during storage or use of the device.

19. A dispenser device according to claim 1, wherein crosslinking in said carbon layer is at least 90%.

20. A dispenser device according to claim 1, wherein crosslinking in said carbon layer is at least 95%.

21. A dispenser device according to claim 1, wherein the carbon layer has a thickness of between 50 nm and 150 nm.

22. A dispenser device according to claim 1, wherein the carbon layer comprises less than about 2 At % oxygen as measured by XPS.

23. A dispenser device according to claim 1, wherein the carbon layer comprises less than about 1 At % oxygen as measured by XPS.

24. A dispenser device according to claim 4, wherein crosslinking in said second layer is at least 55%.

* * * * *